United States Patent
Akiyama

(10) Patent No.: US 12,285,249 B2
(45) Date of Patent: Apr. 29, 2025

(54) INSERTION DEVICE

(71) Applicant: TERUMO KABUSHIKI KAISHA, Tokyo (JP)

(72) Inventor: Takeshi Akiyama, Chuo (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 765 days.

(21) Appl. No.: 17/513,508

(22) Filed: Oct. 28, 2021

(65) Prior Publication Data
US 2022/0047189 A1 Feb. 17, 2022

Related U.S. Application Data

(63) Continuation of application No. PCT/JP2020/030088, filed on Aug. 5, 2020.

(30) Foreign Application Priority Data

Aug. 29, 2019 (JP) ................. 2019-157203

(51) Int. Cl.
*A61B 5/145* (2006.01)
*A61B 5/00* (2006.01)

(52) U.S. Cl.
CPC ........ *A61B 5/14503* (2013.01); *A61B 5/6848* (2013.01); *A61B 5/688* (2013.01)

(58) Field of Classification Search
CPC ... A61B 5/14503; A61B 5/6848; A61B 5/688; A61B 5/14532; A61B 5/14539; A61B 5/14542; A61B 5/14546; A61B 5/1473; A61B 2560/0412
See application file for complete search history.

(56) References Cited

U.S. PATENT DOCUMENTS

| 10,898,115 B2 | 1/2021 | Halac et al. |
| 2017/0182247 A1 | 6/2017 | Fujita |
| 2017/0188910 A1* | 7/2017 | Halac ................. A61B 5/14546 |

(Continued)

FOREIGN PATENT DOCUMENTS

| CN | 106913347 A | 7/2017 |
| CN | 107949314 A | 4/2018 |
| JP | 2019-507613 A | 3/2019 |

(Continued)

OTHER PUBLICATIONS

Chinese Office Action issued in connection with CN Appl. No. 202080012190.2 dated Mar. 14, 2023.

(Continued)

*Primary Examiner* — Michael R Bloch
*Assistant Examiner* — Abid A Mustansir
(74) *Attorney, Agent, or Firm* — Foley & Lardner LLP

(57) ABSTRACT

An insertion device is an insertion device configured to insert a medical device into a living body, including a needle portion to which at least a portion of the medical device is adhered and being inserted into the living body together with the adhered medical device; and a movable portion configured to be movable relatively to the needle portion in a direction of insertion of the needle portion, wherein the movable portion moves relatively to the needle portion in the direction of insertion to cut an adhered region between the medical device and the needle portion and separate the medical device and the needle portion.

7 Claims, 13 Drawing Sheets

(56) References Cited

U.S. PATENT DOCUMENTS

2017/0319137 A1* 11/2017 Tsubouchi ........... A61B 5/6849

FOREIGN PATENT DOCUMENTS

| WO | WO-2014/162383 A1 | 10/2014 |
| WO | WO-2016/120920 A1 | 8/2016 |
| WO | WO-2018/218236 A1 | 11/2018 |

OTHER PUBLICATIONS

Supplemental European Search Report in EP Appl. No. 20857821.1 dated Aug. 25, 2022.

International Searching Authority, "International Search Report," issued in connection with International Patent Application No. PCT/JP2020/030088, dated Sep. 8, 2020.

International Searching Authority, "Written Opinion," issued in connection with International Patent Application No. PCT/JP2020/030088, dated Sep. 8, 2020.

International Searching Authority, "Written Opinion," issued in connection with PCT Application No. PCT/JP2020/030088, dated Sep. 8, 2020 (7 pages).

\* cited by examiner

[FIG. 1]
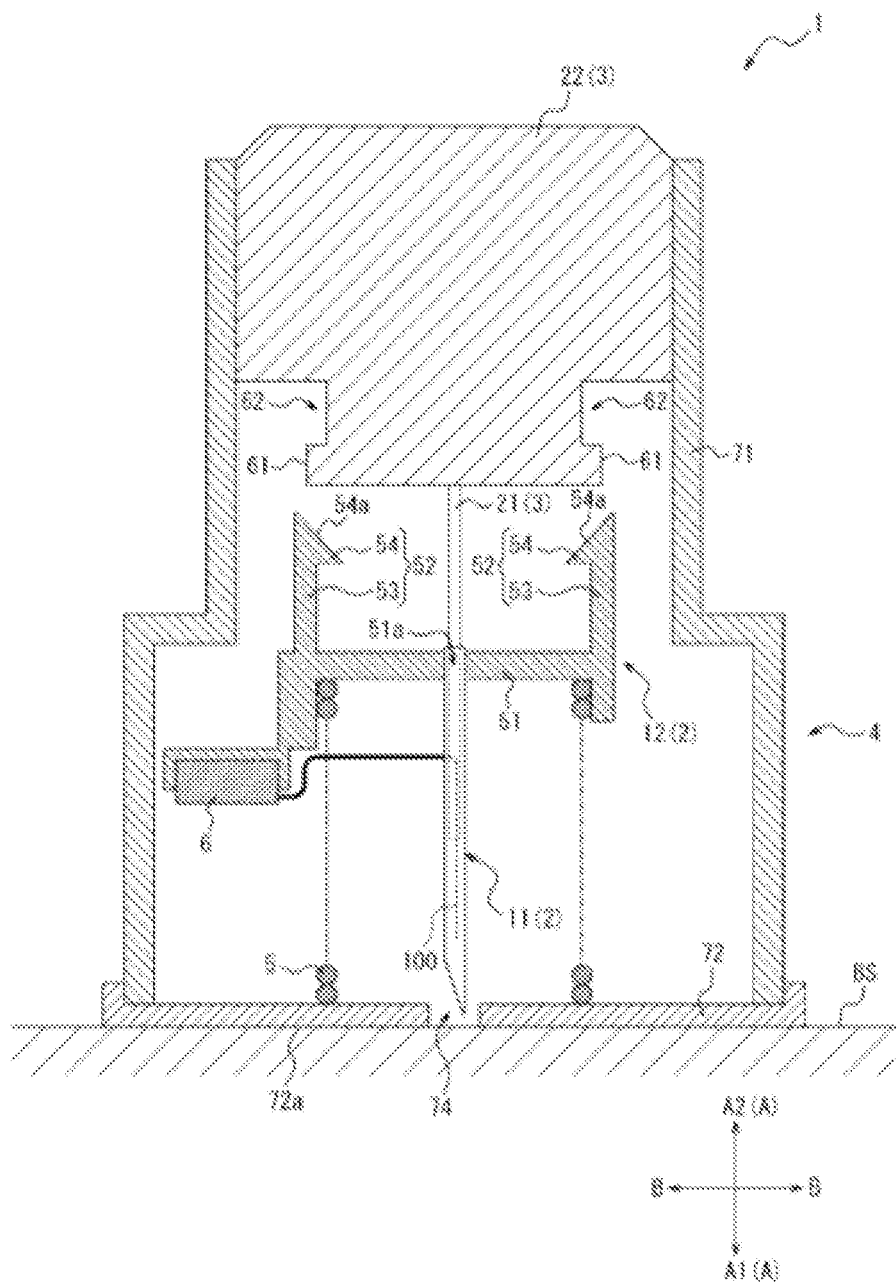

[FIG. 2]
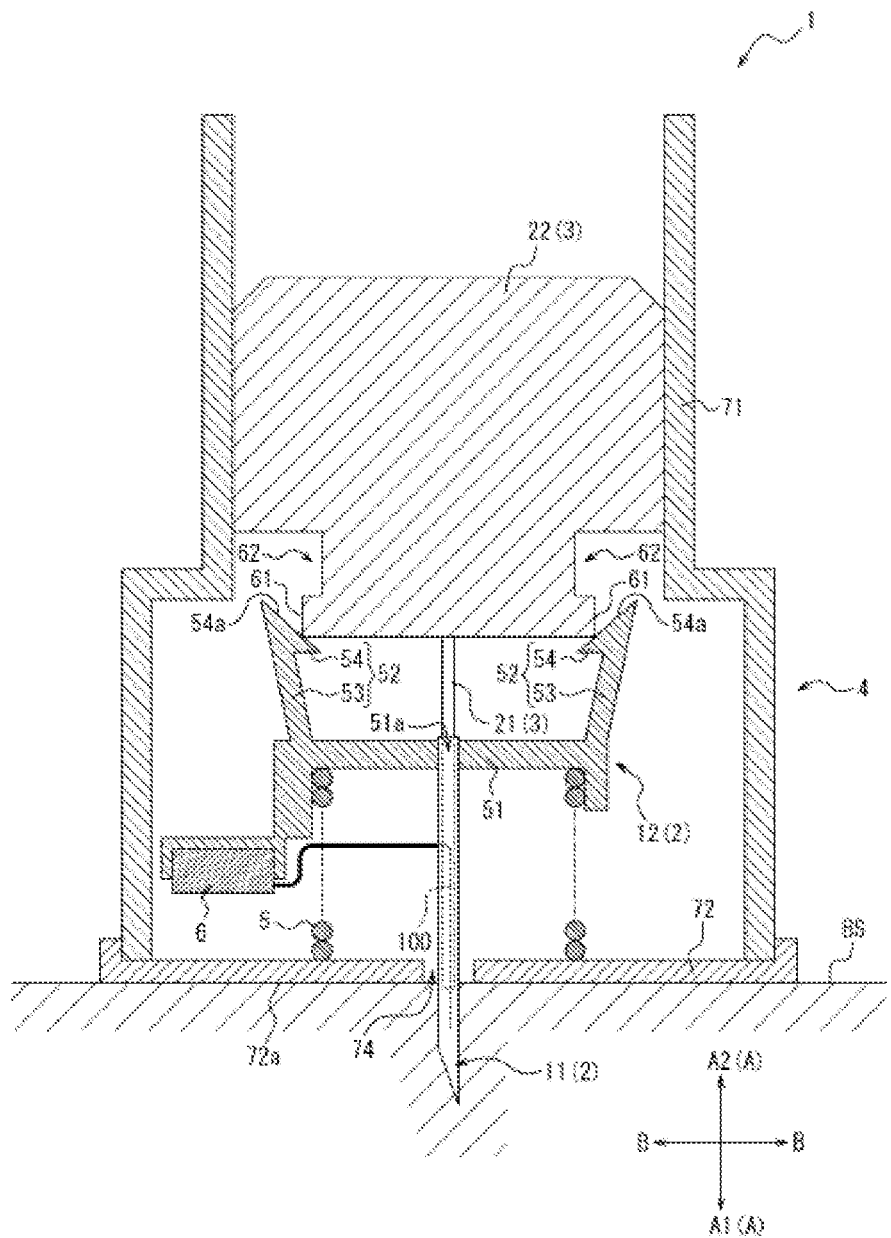

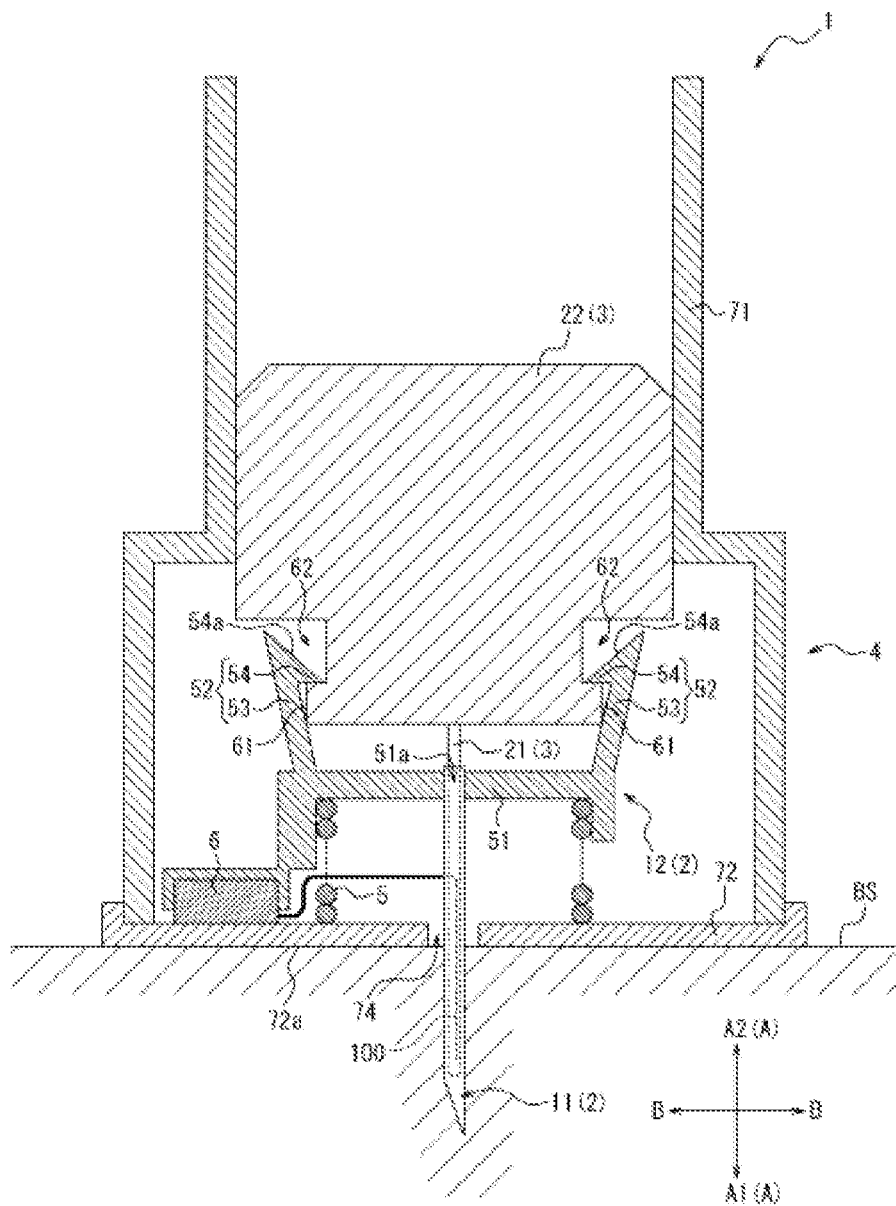
[FIG. 3]

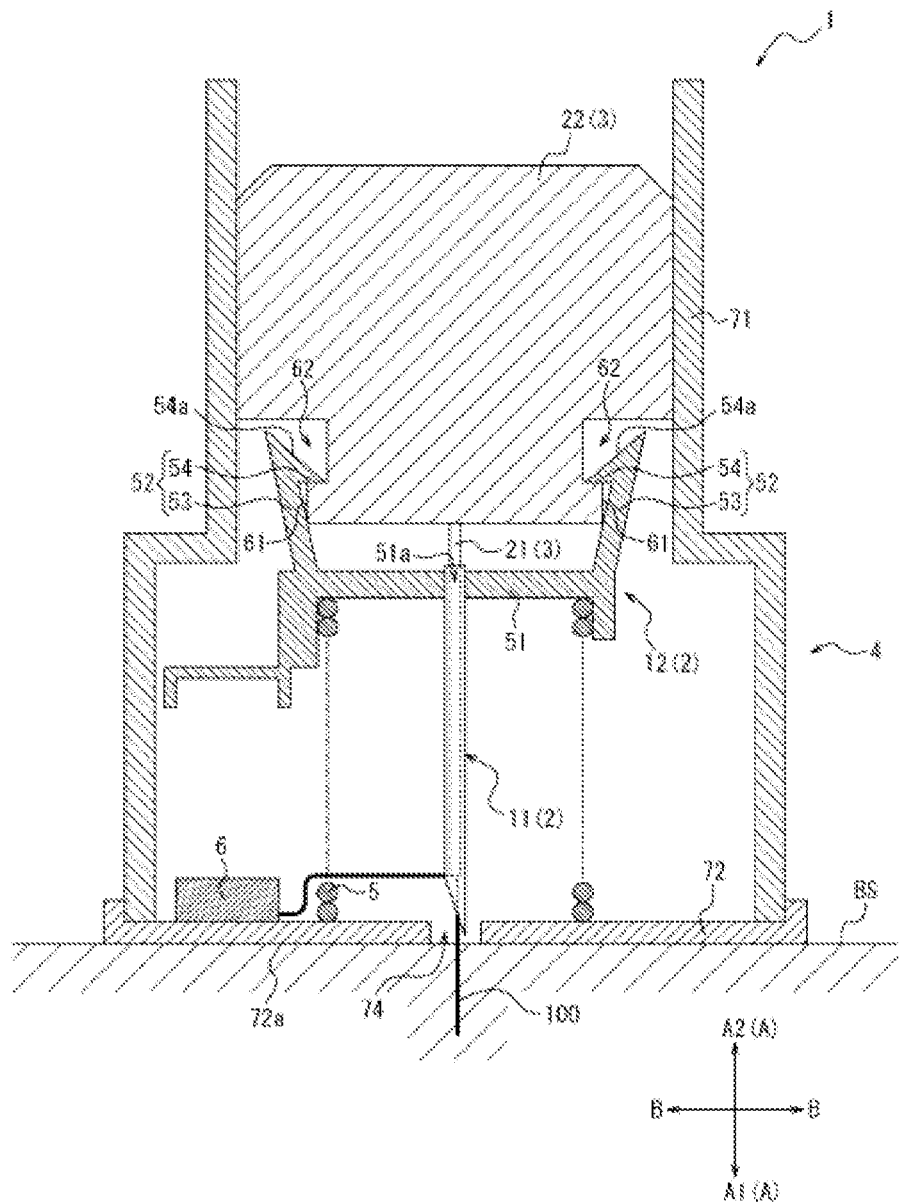
[FIG. 4]

[FIG. 5]
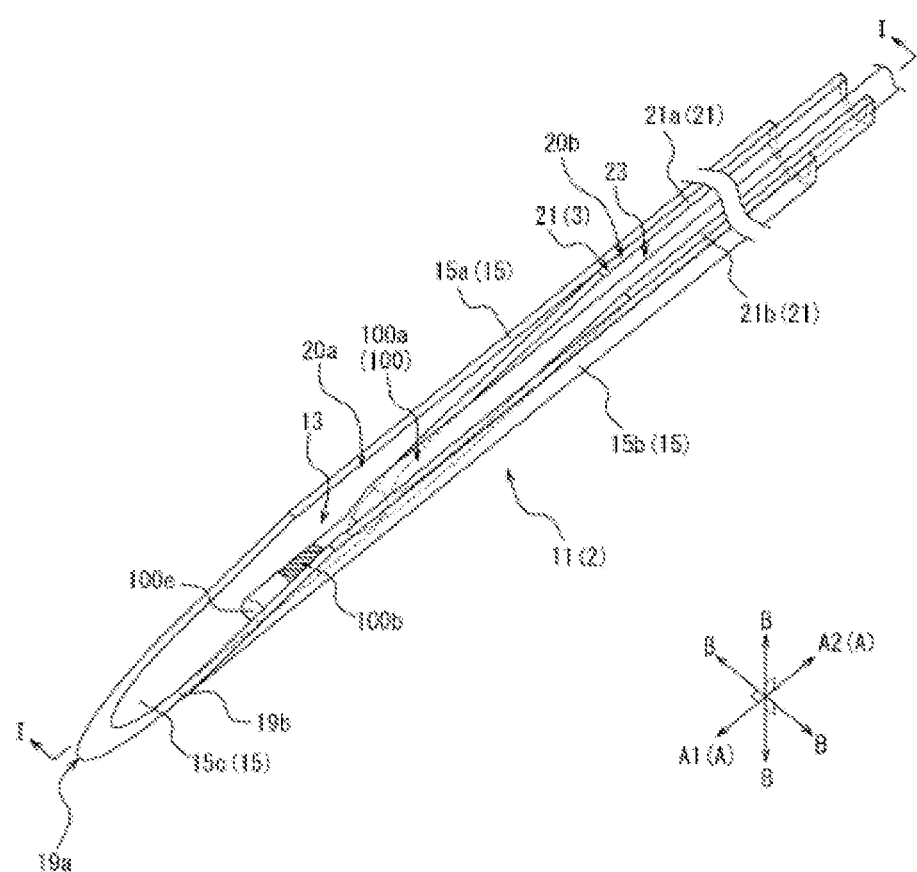

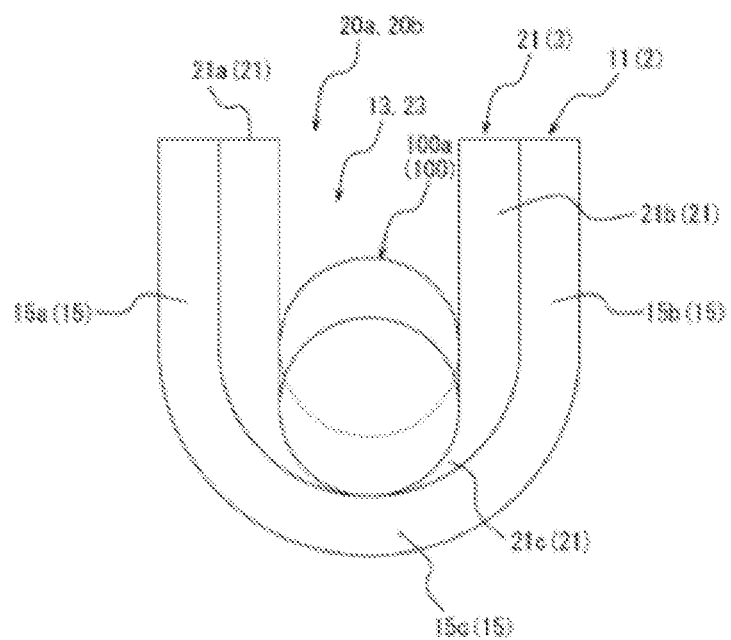

[FIG. 7A]
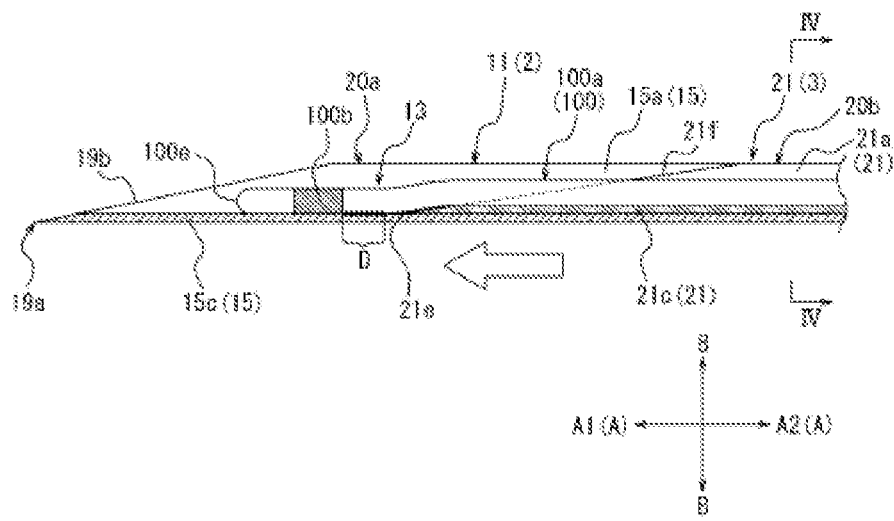
[FIG. 7B]
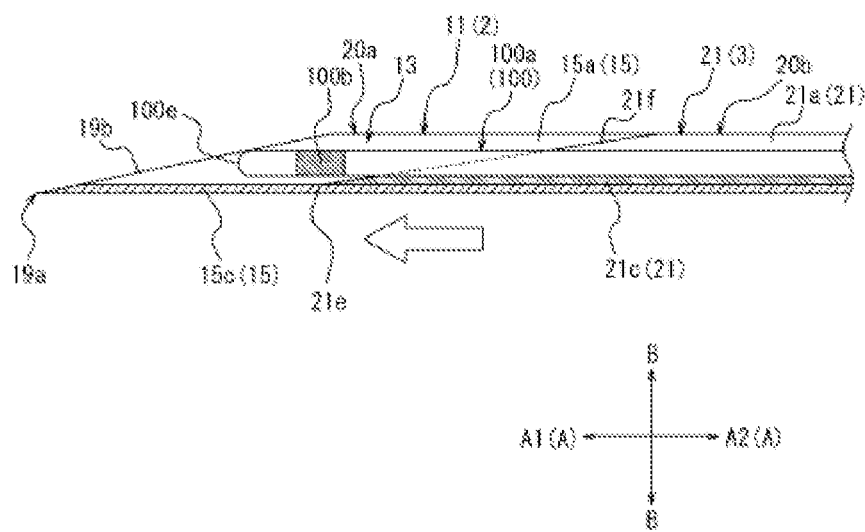

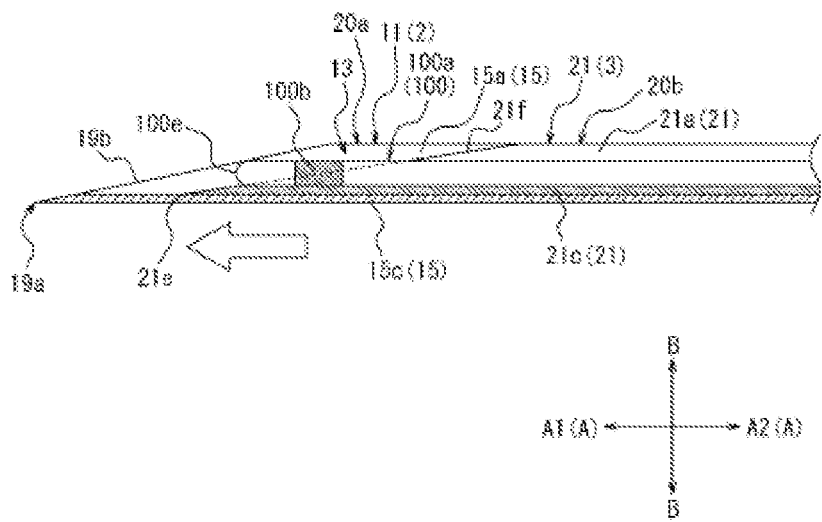
[FIG. 7C]
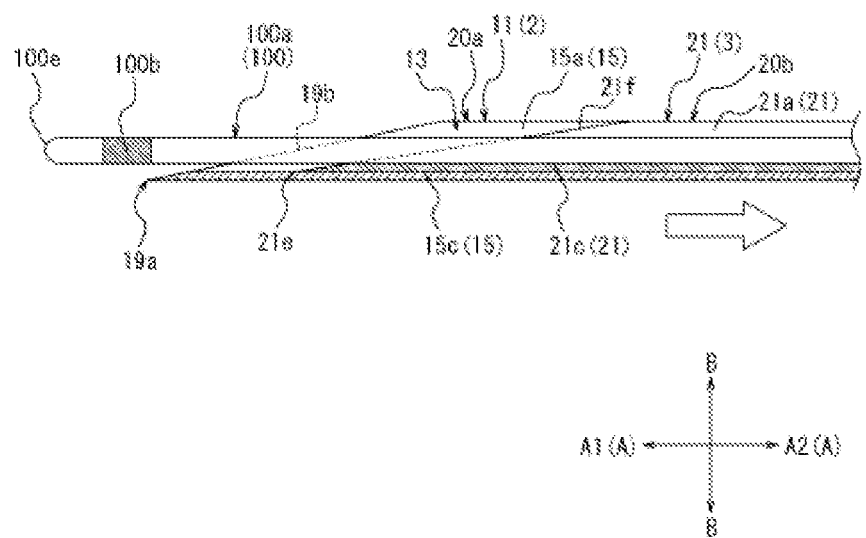
[FIG. 7D]

[FIG. 8]
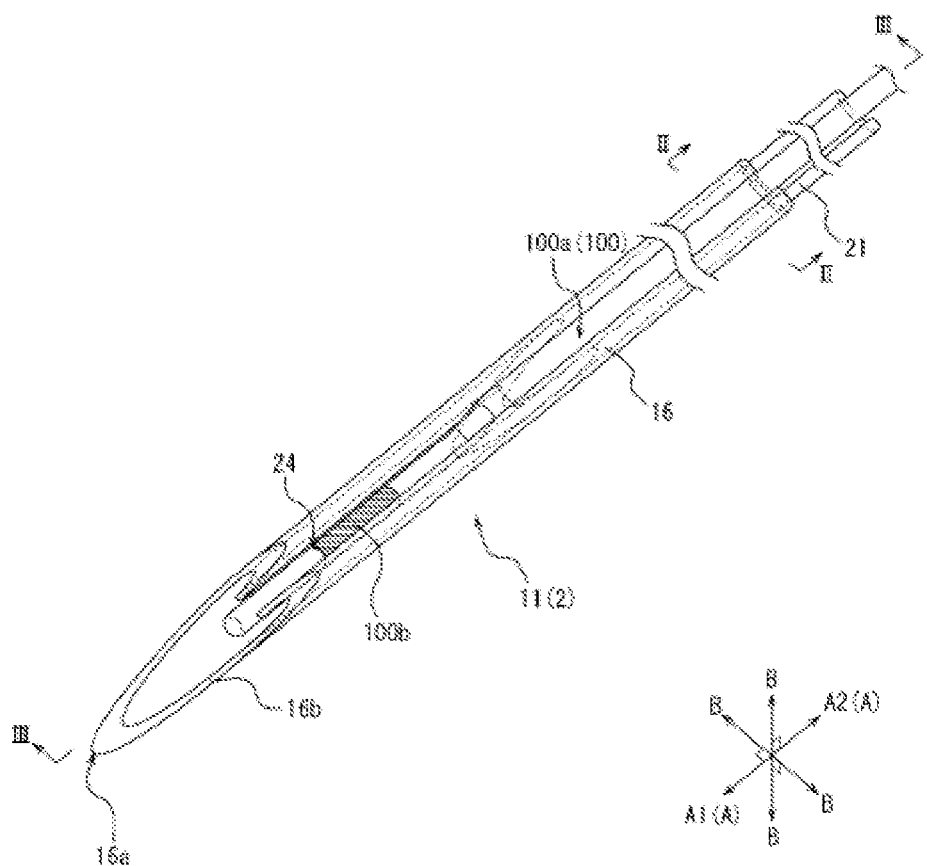

[FIG. 9]
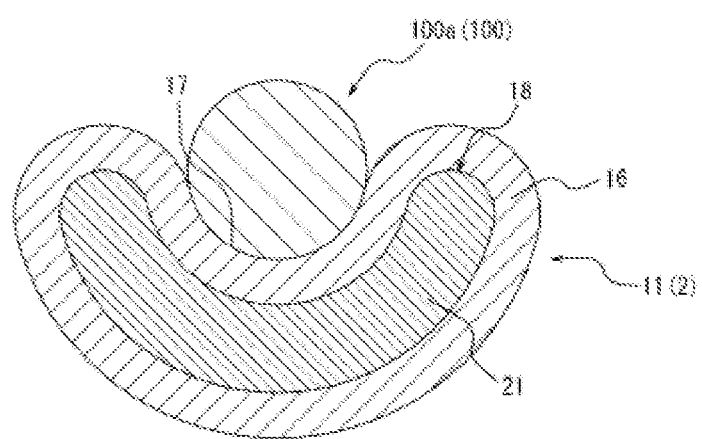

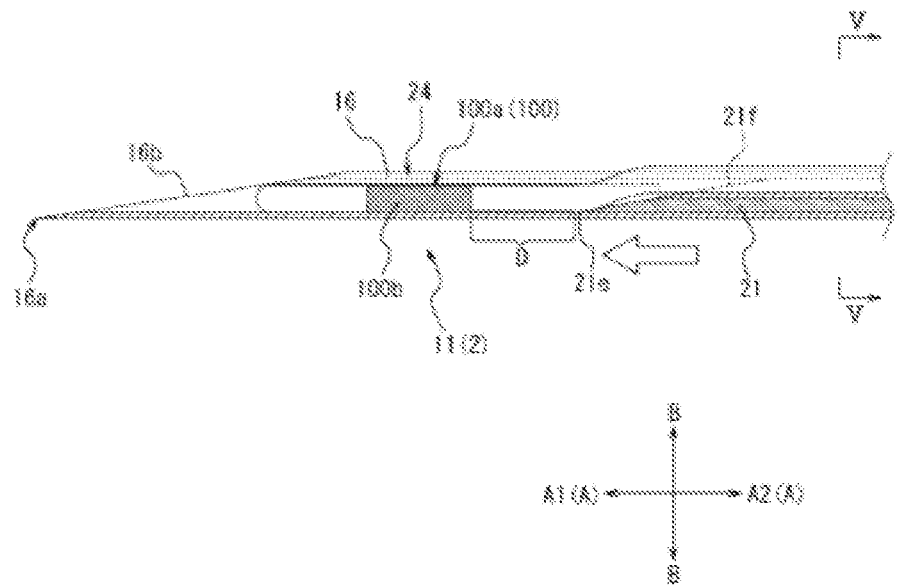
[FIG. 10A]
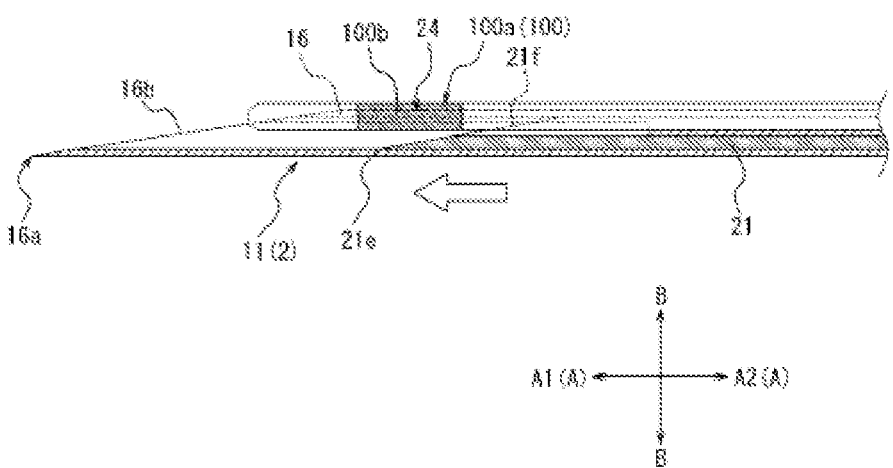
[FIG. 10B]

[FIG. 10C]
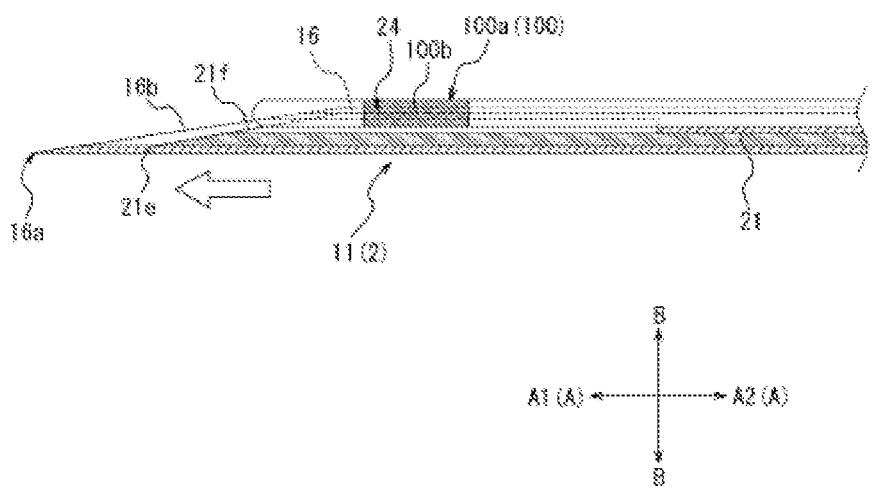
[FIG. 10D]
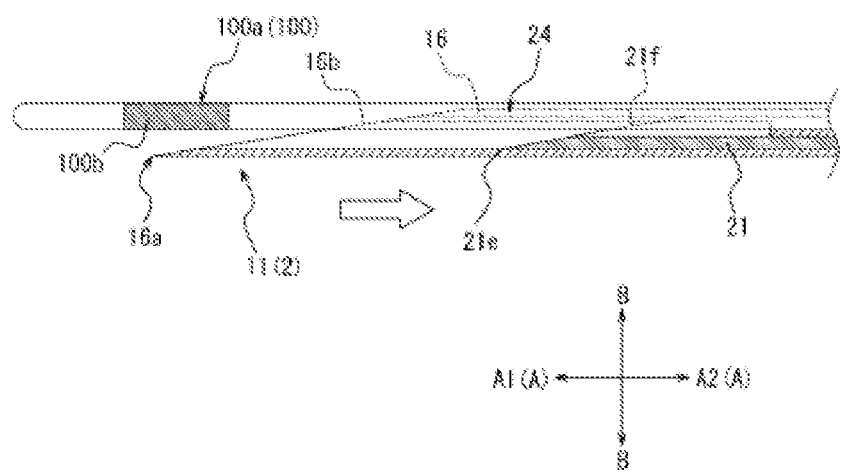

[FIG. 11]
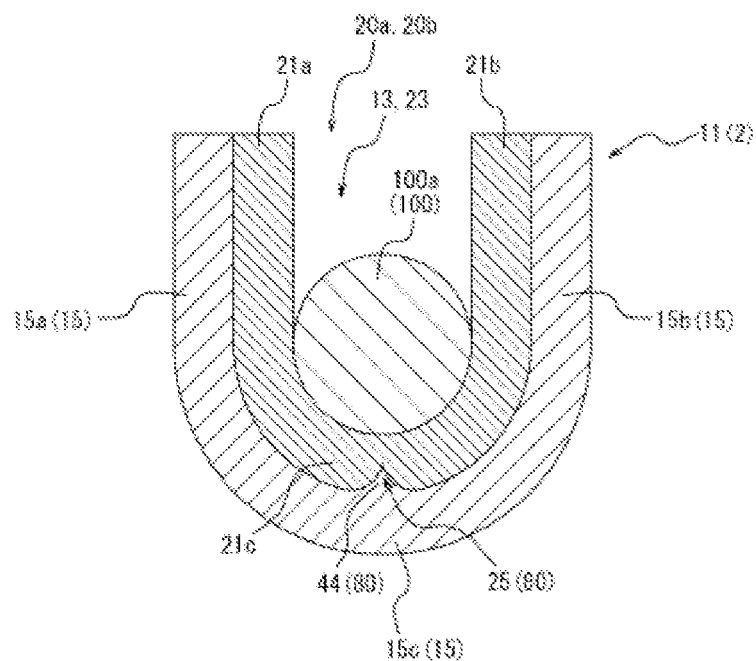
[FIG. 12]
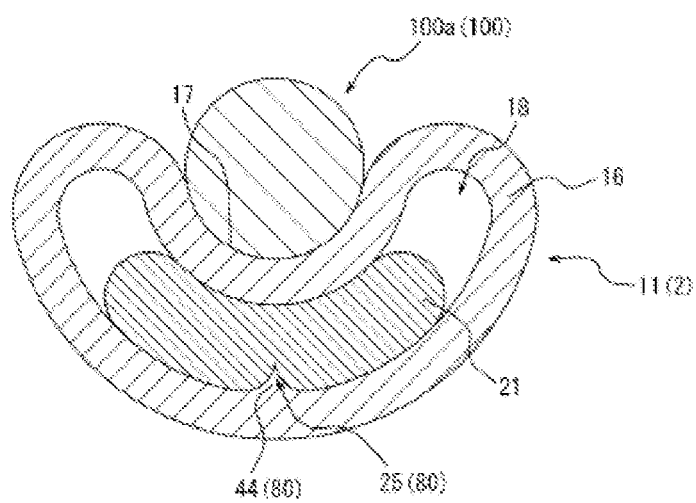

INSERTION DEVICE

CROSS-REFERENCE TO RELATED APPLICATION

The present application is a bypass continuation of PCT Application No. PCT/JP2020/030088, filed on Aug. 5, 2020, which claims priority to Japanese Application No. 2019-157203 filed on Aug. 29, 2019. The contents of these applications are hereby incorporated by reference in their entireties.

BACKGROUND

The present disclosure relates to an insertion device.

Conventionally, a medical device such as a sensor may be implanted in a living body of a subject such as a patient. In one example, a sensor is implanted in a living body of the subject to monitor analytes (for example, glucose, pH, cholesterol, protein, and the like) in blood or in a body fluid of the subject. In this case, an insertion device is used to quickly and easily implant a sensor in the living body through the skin of the subject (see JP-T-2019-507613). The insertion device described in JP-T-2019-507613 is configured to insert the sensor into the living body together with a needle portion, implant the sensor, and then remove only the needle portion from the living body.

SUMMARY

In JP-T-2019-507613, for embedding the sensor in the living body, a gluing agent, for example, is used to adhere an insertion member and the medical device together. In this state, the medical device is inserted into the living body together with the insertion member, and a bonded portion is broken by removing the insertion member from the living body so that the medical device can be implanted in the living body. However, according to this method, whether or not the medical device can be implanted at a desired position in the living body depends on adhesive performance. For example, when the adhesion is too week, the medical device may be detached from the insertion member before the medical device is placed at a desired position so that the medical device cannot be implanted at a desired position in the living body. In contrast, when the adhesion is too strong, the medical device is difficult to separate from the insertion member. In this case as well, the medical device may not be implanted at a desired position in the living body.

The present disclosure is intended to provide an insertion device configured to achieve implantation of a medical device at a desired depth easily in a living body.

According to a first embodiment, an insertion device for inserting a medical device into a living body includes a needle portion to which at least portion of the medical device is adhered and being inserted into the living body together with the adhered medical device; and a movable portion configured to be movable relative to the needle portion in a direction of insertion of the needle portion, wherein the movable portion moves relative to the needle portion in the direction of insertion to cut an adhered region between the medical device and the needle portion and separate the medical device and the needle portion.

According to one aspect, the needle portion internally defines a medical device accommodation space that can accommodate the medical device.

According to another aspect, the needle portion has a sidewall portion that defines the medical device accommodation space, and the medical device is adhered to an inner surface of the sidewall portion.

According to another aspect, the movable portion has a groove space extending along the direction of insertion that is located within the medical device accommodation space and can accommodate the medical device.

According to another aspect, the needle portion is formed into a tubular shape extending along the direction of insertion by a wall portion, and the wall portion has a movable portion accommodation space inside that can accommodate the movable portion.

According to another aspect, the wall portion has a loading surface on a portion of an outer peripheral surface for placing at least a portion of the medical device that is not adhered to the needle portion.

According to another aspect, a restricting mechanism is provided to restrict relative movement of the needle portion and the movable portion in directions other than a longitudinal direction of the needle portion.

According to certain embodiments of the present disclosure, an insertion device configured to easily achieve implantation of a medical device at a desired depth in a living body is provided.

BRIEF DESCRIPTION OF THE DRAWINGS

FIG. 1 is a drawing illustrating an insertion device according to a first embodiment of the present disclosure and a state in which a needle portion is located in awaiting position.

FIG. 2 is a drawing illustrating a state in which the needle portion of the insertion device illustrated in FIG. 1 is in the course of moving from the waiting position to an insertion position.

FIG. 3 is a drawing illustrating a state in which the needle portion of the insertion device illustrated in FIG. 1 is in the insertion position.

FIG. 4 is a drawing illustrating a state in which the needle portion of the insertion device illustrated in FIG. 1 is removed from the insertion position to outside of a living body.

FIG. 5 is a perspective view illustrating the needle portion, a movable portion, and a medical device according to the first embodiment in the insertion device in the state illustrated in FIG. 1.

FIG. 6 is a drawing of the needle portion, the movable portion, and a sensor illustrated in FIG. 5 viewed from a distal side.

FIG. 7A is a cross-sectional view taken along a line I-I in FIG. 5 illustrating the needle portion, the movable portion, and the medical device in the state in which the needle portion of the insertion device illustrated in FIG. 1 is in the waiting position.

FIG. 7B is a cross-sectional view taken along a line I-I in FIG. 5 illustrating the needle portion, the movable portion, and the medical device in the state in which the needle portion is in the course of moving from the waiting position to the insertion position.

FIG. 7C is a cross-sectional view taken along a line I-I in FIG. 5 illustrating the needle portion, the movable portion, and the medical device in the state in which the needle portion is in the insertion position.

FIG. 7D is a cross-sectional view taken along a line I-I in FIG. 5 illustrating the needle portion, the movable portion, and the medical device in a state in which the needle portion is in the course of returning back into a housing after implanting the medical device in the insertion position.

FIG. 8 is a perspective view illustrating a needle portion of a needle member, a movable portion of a movable member, and a medical device in an insertion device according to a second embodiment of the present disclosure.

FIG. 9 is a cross-sectional view taken along a line II-II in FIG. 8 in which the needle portion, the movable portion, and the medical device are orthogonal to a longitudinal direction.

FIG. 10A is a cross-sectional view taken along the line III-III in FIG. 8 illustrating the needle portion, the movable portion, and the medical device in the state in which the needle portion of the insertion device illustrated in FIG. 1 is in the waiting position.

FIG. 10B is a cross-sectional view taken along the line III-III in FIG. 8 illustrating the needle portion, the movable portion, and the medical device in the state in which the needle portion is in the course of moving from the waiting position to the insertion position.

FIG. 10C is a cross-sectional view taken along the line III-III in FIG. 8 illustrating the needle portion, the movable portion, and the medical device in the state in which the needle portion is in the insertion position.

FIG. 10D is a cross-sectional view taken along the line III-III in FIG. 8 illustrating the needle portion, the movable portion, and the medical device in the state in which the needle portion is in the course of returning back into a housing after implanting the medical device in the insertion position.

FIG. 11 is a cross-sectional view taken along a line IV-IV in FIG. 7A.

FIG. 12 is a cross-sectional view taken along a line V-V in FIG. 10A.

DETAILED DESCRIPTION

Referring now to drawings, embodiments of the present invention will be described. The same reference numerals are given to common constituent parts in the drawings.

First Embodiment

FIG. 1 to FIG. 4 illustrate an insertion device 1 according to a first embodiment of the present disclosure. In addition, as will be described in detail below, FIG. 1 to FIG. 4 each illustrate an overview of an operation of the insertion device 1 when inserting and implanting a medical device 100 in a living body using the insertion device 1. The insertion device 1 illustrated in FIG. 1 to FIG. 4 can insert a sensor 100a as the medical device 100 into the living body. Hereinafter, in the present embodiment, the insertion device 1 configured to insert the sensor 100a as the medical device 100 into the living body will be described. However, the medical device 100 to be inserted into the living body by the insertion device 1 is not limited to the sensor 100a. Therefore, the insertion device may be configured to insert a tubular member other than the sensor, such as a cannula.

As illustrated in FIG. 1 to FIG. 4, the insertion device 1 includes a needle member 2, a movable member 3, a housing 4, a biasing member 5, a controller 6, and the sensor 100a as the medical device 100. As illustrated in FIG. 1 to FIG. 4, the needle member 2 of the present embodiment includes a needle portion 11 and a holding portion 12. The movable member 3 of the present embodiment includes a movable portion 21 and a main body portion 22.

Referring now to FIG. 1 to FIG. 4, a method of using the insertion device 1 of the present embodiment will be described. The insertion device 1 of the present embodiment may be used for inserting and implanting the sensor 100a in the living body as described above. The insertion device 1 is disposed on a living body surface BS in a state illustrated in FIG. 1. In other words, FIG. 1 illustrates a state before the needle portion 11 of the needle member 2 and the sensor 100a are inserted into a living body. Then, an operator such as a health care worker operates the insertion device 1 to insert the needle portion 11 of the needle member 2 and the sensor 100a into the living body (See FIG. 2 and FIG. 3). FIG. 2 is a drawing illustrating a state in the course of inserting the needle portion 11 and the sensor 100a into the living body by the insertion device 1. FIG. 3 is a drawing illustrating a state in which the needle portion 11 and the sensor 100a reach the deepest possible position in the living body where the insertion device 1 can be inserted. Next, as illustrated in FIG. 4, the needle portion 11 of the needle member 2 is removed to outside of the living body with the sensor 100a left in the living body. In this manner, the sensor 100a can be inserted and implanted into the living body by the insertion device 1. For the sake of convenience of explanation, the position of the needle portion 11 in FIG. 1 where the needle portion 11 is accommodated in the housing 4 is referred to as "a (the) waiting position of the needle portion 11", hereinafter. Likewise, for the sake of convenience of explanation, the position of the needle portion 11 in FIG. 3 where the needle portion 11 protrudes the most from the housing 4 is referred to as "a (the) insertion position of the needle portion 11", hereinafter.

The sensor 100a to be implanted in the living body detects a substance to be measured (analyte) and transmits information of a detection result to, for example, the controller 6. The controller 6 is connected to the sensor 100a via a cable and is implanted on the living body surface BS together with the sensor 100a. The controller 6 includes a processor, a memory, and a battery. The sensor 100a of the present embodiment illustrated in FIG. 1 to FIG. 4 transmits the information of the detection result to the controller 6. By using the sensor 100a together with the controller 6, a signal can be detected according to the concentration of the substance to be measured. The detected signal is processed by the controller 6 and is transmitted to a smartphone or a dedicated terminal of a subject. The subject or the user can confirm the result of measurement of the substance to be measured displayed on a screen of the smartphone or the dedicated terminal with time. A time period during which the sensor 100a is attached to the subject is determined as appropriate in the determination of the doctor or the like, such as several hours, several days, a week, a month, and so forth. Although the substance to be measured is not particularly limited, for example, glucose, oxygen, pH, lactic acid, or the like in the blood or an interstitial fluid can be measured according to the selection of the detection portion of the sensor 100a. Note that the controller 6 may be connected to a separately provided transmitter (not illustrated) after the completion of insertion of the sensor 100a. In this case, instead of the controller 6, the transmitter may be configured to have a memory, a battery, and the like. The transmitter may be configured to be used for a longer period than the sensor 100a.

The details of each member and each portion of the insertion device 1 will be described below.

FIG. 5 is a perspective view illustrating the needle portion 11 of the needle member 2, the movable portion 21 of the movable member 3, and sensor 100a in the insertion device 1 in the state illustrated in FIG. 1.

Hereinafter, in this specification, an end of the needle portion 11 of the needle member 2 to be inserted into the living body will be referred to as "a (the) distal end of the needle portion 11". Also, an opposite end from the distal end of the needle portion 11 of the needle member 2 is referred to as "a (the) proximal end of the needle portion 11". Further, a direction from the proximal end toward the distal end of a longitudinal direction A of the needle portion 11 of the needle member 2 is referred to as "direction of insertion A1" or "distal side". Further, a direction from the distal end toward the proximal end of the longitudinal direction A of the needle portion 11 of the needle member 2 is referred to as "direction of removal A2" or "proximal side". A radial direction B of the needle portion 11 refers to a radial direction of a circle, which is defined on a plane orthogonal to the longitudinal direction A. of the needle portion 11 around the needle portion 11 with a center at the needle portion 11. An outward direction from a central axis of the needle portion 11 of the needle member 2 is referred to as "outward in the radial direction B". A direction toward the central axis of the needle portion 11 from a circumference of the circle, which is defined around the needle portion 11 of the needle member 2, is referred to as "inside in the radial direction B". Note that the "circle around the needle portion 11 of the needle member 2" substantially corresponds to an inner peripheral surface of a third side plate portion 15*c* in a cross section of the needle portion 11, when the third side plate portion 15*c* is formed into an arcuate shape. When the third side plate portion 15*c* is not formed into the arcuate shape, the center of the circle around the needle portion 11 of the needle member 2 is present at an equal distance from both end portions of the third side plate portion 15*c* (end portions of the third side plate portion 15*c* connected respectively to a first side plate portion 15*a* and a second side plate portion 15*b*), described below, in a cross section orthogonal to the longitudinal direction A of the needle portion 11.

FIG. 6 is a drawing of the needle portion 11, the movable portion 21, and the sensor 100*a* illustrated in FIG. 5 viewed from a distal side. FIG. 7A is a cross-sectional view taken along the line I-I in FIG. 5 illustrating the needle portion 11, the movable portion 21, and the medical device 100 in the state in which the needle portion 11 of the insertion device 1 illustrated in FIG. 1 is in the waiting position.

As illustrated in FIG. 5 to FIG. 7A, the needle portion 11 internally defines a medical device accommodation space 13 that can accommodate the medical device 100. The needle portion 11 is inserted into the living body together with the medical device 100 to be accommodated in the medical device accommodation space 13.

As illustrated in FIG. 5 and FIG. 6, the needle portion 11 of the present embodiment includes a sidewall portion 15 that defines the medical device accommodation space 13.

The sidewall portion 15 of the present embodiment includes the first side plate portion 15*a* and the second side plate portion 15*b* arranged to face each other, and the third side plate portion 15*c* continuing to the respective end portions of the first side plate portion 15*a* and the second side plate portion 15*b* on one side. The first side plate portion 15*a*, the second side plate portion 15*b*, and the third side plate portion 15*c* define the medical device accommodation space 13.

The sidewall portion 15 extends in the longitudinal direction A. In the present embodiment, the first side plate portion 15*a* and the second side plate portion 15*b* are each made of an elongated flat plate extending in the longitudinal direction A. Also, in the present embodiment, the third side plate portion 15*c* extends in the longitudinal direction A together with the first side plate portion 15*a* and the second side plate portion 15*b*. The third side plate portion 15*c* is made of an arcuate shaped plate in cross section orthogonal to the longitudinal direction A. The sidewall portion 15 of the present embodiment forms a U-shaped groove with the first side plate portion 15*a*, the second side plate portion 15*b* and the third side plate portion 15*c*. However, the cross-sectional profile orthogonal to the longitudinal direction A of the sidewall portion 15 is not limited to the shape of the U-shaped groove as in the present embodiment, but may have other cross-sectional profiles, such as a rectangular shape and a C-shape. In such a case, the third side plate portion 15*c* is formed into a suitable shape such as a flat plate shape, a semi-circulate shape, or a substantially semi-circular shape. The first sideplate portion 15*a* and the second side plate portion 15*b* may also be formed into an arcuate shape in cross section. In the present embodiment, the sensor 100*a* is connected to the controller 6 provided on a base plate 72 with a cable. Therefore, owing to the sectional profile of the sidewall portion 15 formed into a U-shape, the sensor 100*a* can be pulled out from the medical device accommodation space 13 on an opening (a needle portion slit 20*a*) side of the U-shape. For example, a configuration in which a separate transmitter (not illustrated) is attached to the base plate 72 having the sensor 100*a* allows for a configuration in which the controller 6 is accommodated in the transmitter, and a connecting point with respect to the sensor 100*a* is provided at any position in the transmitter.

As illustrated in FIG. 5 and FIG. 7A, the distal end portion of the sidewall portion 15 includes a cutting edge 19*a* and a cutting surface 19*b*. The cutting edge 19*a* is formed at a distal end of the distal end portion of the sidewall portion 15. A distal end of the third side plate portion 15*c* of the sidewall portion 15 of the present embodiment constitutes the cutting edge 19*a*. More specifically, the sidewall portion 15 of the present embodiment is provided with the cutting surface 19*b* formed by a bevel inclined with respect to the longitudinal direction A. The cutting surface 19*b* is formed to be tapered toward the cutting edge 19*a*. In the example illustrated in FIG. 5 and FIG. 7A, the cutting surface 19*b* is formed to be inclined in side view of the needle portion 11 viewed from a side of the first sidewall portion 15*a*. The shape of the bevel may be a flat surface or a curved surface. The cutting edge 19*a* of the sidewall portion 15 is not limited to this configuration. For example, the sidewall portion 15 may have a configuration provided with one or more cutting surfaces 19*b* having a distal end inclined with respect to the longitudinal direction A or may be a cutting surface asymmetric with respect to the central axis of the needle portion 11.

In the present embodiment, facing widths of outer surfaces of the first side plate portion 15*a* and the second side plate portion 15*b* of the sidewall portion 15 may be, for example, 0.2 mm to 0.6 mm. A length of the sidewall portion 15 to be inserted into the living body may be, for example, 1 mm to 10 mm, preferably 3 to 6 mm. A thickness of the first side plate portion 15*a*, the second side plate portion 15*b*, and the third side plate portion 15*c* may be set from a range, for example, from 0.02 mm to 0.15 mm.

As illustrated in FIG. 5 and FIG. 7A, a detection portion 100*b* of the sensor 100*a* is provided in the vicinity of a distal end 100*e* of the sensor 100*a*. To protect the detection portion 100*b*, the detection portion 100*b* is preferably provided rather on a proximal side of the distal end 100*e*.

The medical device 100 is at least partly fixed to the needle portion 11. In the present embodiment, at least a portion of the sensor 100*a* as the medical device 100 is fixedly adhered to the sidewall portion 15. Specifically, as illustrated in FIG. 5 to FIG. 7A, the sensor 100a is partly fixedly adhered to the third side plate portion 15c.

In the present embodiment, a portion of the sensor 100a on the proximal side of the detection portion 100b is fixedly adhered to the third side plate portion 15c of the sidewall portion 15. A region where the sensor 100a and the third side plate portion 15c are fixedly adhered is indicated as an adhered region D in FIG. 7A. The adhered region D corresponds to at least a portion of a side surface of the sensor 100a that comes into contact with the sidewall portion 15, and to a region fixed to the sidewall portion 15. An adhesive agent is applied on the surface of the sensor 100a corresponding to the adhered region D. By fixedly adhering the sensor 100a and the third side plate portion 15c, the sensor 100a is stably held in the needle portion 11. Accordingly, the sensor 100a may be inserted to a desired depth in the living body together with the needle portion 11. A type of the adhesive agent used here may be of any type having biocompatibility, and an amount of the adhesive agent may be any amount that can maintain the adhesive strength required for inserting the sensor 100a and the needle portion 11 into the living body.

Examples of the material of the needle portion 11 that can be used include a metallic material such as stainless steel, aluminum, aluminum alloy, titanium, titanium alloy, and magnesium alloy. The material of the needle portion 11 is selected from those that allow for manufacturing by plastic working. Examples of the plastic working include cutting work on a drawn tube having a predetermined inner diameter or press work on a metallic plate. Preferably, the material that can be applied to the press work is selected as the material of the needle portion 11.

The holding portion 12 holds the proximal end portion of the needle portion 11. The holding portion 12 of the present embodiment includes a main body portion 51 and a locking claw portion 52. The main body portion 51 is provided with a holding opening 51a penetrating in the longitudinal direction A. The proximal end portion of the needle portion 11 is fixed to the main body portion 51 in a state of being inserted in the holding opening 51a. The locking claw portion 52 projects from the main body portion 51 toward the direction of removal A2. The locking claw portion 52 is positioned outside the needle portion 11 in the radial direction B of the needle portion 11. Also, the needle member 2 of the present embodiment is provided with a plurality of the locking claw portions 52 so as to surround the periphery of the needle portion 11 outside the needle portion 11 in the radial direction B. The locking claw portions 52 each include an extending portion 53 protruding from the main body portion 51 and an engagement projection 54 provided at an end portion of the extending portion 53 in the direction of removal A2. The extending portion 53 is resiliently deformable in a direction orthogonal to the longitudinal direction A with the position continuing to the main body portion 51 as a fulcrum. More specifically, the extending portion 53 of the present embodiment is resiliently deformable in the radial direction B of the needle portion 11 with the position continuing to the main body portion 51 as a fulcrum. The engagement projection 54 protrudes in the direction orthogonal to the longitudinal direction A from the end portion of the extending portion 53. An upper surface 54a located in the direction of removal A2 of each engagement projection 54 is inclined with respect to the longitudinal direction A so as to extend inward in the radial direction B as it proceeds the direction of insertion A1. The upper surfaces 54a of the engagement projections 54 are pressed outward in the radial direction B by being engaged with the main body portion 22, described below, of the movable member 3. Detail description will be given below.

Examples of the material of the holding portion 12 include a resin material. Examples of the resin material include: thermoplastic resins used in injection molding such as ABS resin, AS resin, polyethylene, polypropylene, polystyrene, polyvinyl chloride, polyvinylidene chloride resin, polyphenylene oxide, thermoplastic polyurethane, polymethylene methacrylate, polyoxyethylene, fluorine resin, polycarbonate, polyamide, acetal resin, acrylic resin, and polyethylene terephthalate; and thermosetting resins such as phenol resin, epoxy resin, silicone resin, and unsaturated polyester.

As described above, the movable member 3 of the present embodiment includes the movable portion 21 and the main body portion 22.

The movable portion 21 is movable relatively with respect to the needle portion 11 in the medical device accommodation space 13 in the direction of insertion A1 of the needle portion 11. The movable portion 21 cuts the adhered region D between the medical device 100 and the needle portion 11 by moving in the direction of insertion A1 with respect to the needle portion 11. Specifically, a distal end 21e of the movable portion 21 comes into contact with the adhered region D from the proximal end portion side to separate the medical device 100 and the needle portion 11 in the adhered region D. Accordingly, an adhered state between the medical device 100 and the needle portion 11 is released, and thus the fixation of the medical device 100 with respect to the needle portion 11 is released. Specifically, the movable portion 21 of the present embodiment moves in the direction of insertion A1 with respect to the needle portion 11. A cutting edge 21e that constitutes the distal end of the movable portion 21 comes into contact with the proximal end of the adhered region D. From this state, the movable portion 21 further moves in the direction of insertion A1 so that the medical device 100 and the needle portion 11 are separated from the proximal end to the distal end of the adhered region D. Accordingly, the fixation of the medical device 100 with respect to the needle portion 11 is released. At this time, the movable portion 21 enters between the medical device 100 and the needle portion 11.

As illustrated in FIG. 5 and FIG. 6, the movable portion 21 of the present embodiment is configured as a member extending in the longitudinal direction A along an inner peripheral surface of the sidewall portion 15 of the needle portion 11 in the medical device accommodation space 13. Specifically, the movable portion 21 extends along the longitudinal direction A of the needle portion 11, and includes a first groove wall portion 21a, a second groove wall portion 21b, and a third groove wall portion 21c. The first groove wall portion 21a and the second groove wall portion 21b are arranged to face each other. The third groove wall portion 21c continues to respective end portions of the first groove wall portion 21a and the second groove wall portion 21b on one side. The first groove wall portion 21a, the second groove wall portion 21b, and the third groove wall portion 21c define a groove space 23. The movable portion 21 is configured to be capable of holding the medical device 100 in the groove space 23. The first groove wall portion 21a and the second groove wall portion 21b are formed of a flat plate, and the third groove wall portion 21c is formed of a plate on an arc.

The movable portion 21 includes a cutting surface 21f formed of a bevel inclining with respect to the longitudinal direction A so that the distal end of the third groove wall portion 21c forms the sharp cutting edge 21e. However, the configuration of the cutting edge 21e of the movable portion 21 is not limited to the configuration of the present embodiment. The cutting edge 21e only needs to be capable of coming into contact with the adhered region D and advancing toward the distal side while separating the adhered region D when the movable portion 21 moves in the direction of insertion A1 with respect to the needle portion 11. This may separate the medical device 100 and the needle portion 11.

Note that the shapes of the first groove wall portion 21a, the second groove wall portion 21b, and the third groove wall portion 21c are not limited to the shapes described above. The first groove wall portion 21a, the second groove wall portion 21b, and the third groove wall portion 21c may be formed into shapes that allow the movable portion 21 to separate the adhered region D. The first groove wall portion 21a, the second groove wall portion 21b, and the third groove wall portion 21c are preferably formed into shapes that make the movable portion 21 conform with the sidewall portion 15 as a whole.

The movable portion 21 includes an opening (movable portion slit 20b) through which a proximal end portion of the sensor 100a as the medical device 100 can be pulled out from the movable portion 21 outward of the movable portion 21 in the same manner as the sidewall portion 15. When the sensor 100a is connected with the controller 6 wirelessly, the movable portion 21 may be formed into a tubular shape having no opening.

Examples of the material of the movable portion 21 that can be used include a metallic material such as stainless steel, aluminum, aluminum alloy, titanium, titanium alloy, and magnesium alloy. The movable portion 21 can be manufactured by plastic working. The movable portion 21 can be manufactured, for example, by cutting work on a drawn tube having a predetermined inner diameter or press work on a metallic plate.

The main body portion 22 holds the end portion of the movable portion 21 in the direction of removal A2. The main body portion 22 of the present embodiment is attached so as to be movable in the longitudinal direction A in the housing 4. The main body portion 22 of the present embodiment has an upper surface in the direction of removal A2 exposed from the housing 4 to the outside. Therefore, the operator of the insertion device 1 can move the main body portion 22 in the direction of insertion A1 by pressing the main body portion 22 exposed from the housing 4 in the direction of insertion A1. Accordingly, the movable portion 21 attached to the main body portion 22 can also move in the medical device accommodation space 13 of the needle portion 11 in the direction of insertion A1. In other words, the main body portion 22 also serves as an operation unit of the insertion device 1.

The main body portion 22 includes an engagement portion 61 configured to press the locking claw portions 52 of the holding portion 12 of the needle member 2 outward in the radial direction B of the needle portion 11. The main body portion 22 defines an engagement depression 62, in which the engagement projection 54 of the locking claw portion 52 can fit, at a position adjacent to the engagement portion 61 in the direction of removal A2. The engagement depression 62 is depressed inward with respect to the engagement portion 61 in the radial direction B. As illustrated in FIG. 1 to FIG. 4, the engagement portion 61 may be formed, for example, of a disk portion. Also, as illustrated in FIG. 1 to FIG. 4, the engagement depression 62 is formed by an annular groove located adjacent to the disk portion as the engagement portion 61 in the direction of removal A2 and depressed inward with respect to an outer edge of the disk portion in the radial direction B. However, the configurations of the engagement portion 61 and the engagement depression 62 are not limited to the shape and the position illustrated in the present embodiment.

As illustrated in FIG. 1 to FIG. 3, the insertion device 1 of the present embodiment can insert the needle portion 11 and the sensor 100a into the living body by pushing the main body portion 22 in the direction of insertion A1. At that time, the engagement portion 61 of the main body portion 22 engages the upper surfaces 54a located in the direction of removal A2 of the engagement projections 54 of the locking claw portions 52 and presses the engagement projections 54 outward in the radial direction B. Accordingly, as illustrated in FIG. 2, the extending portions 53 of the locking claw portions 52 resiliently deform outward in the radial direction B. In other words, the plurality of engagement claw portions 52 located in the outside periphery of the needle portion 11 in the radial direction B resiliently deform outward in the radial direction B away from each other. Therefore, as illustrated in FIG. 3, the engagement portion 61 of the main body portion 22 can pass over the engagement projections 54 in the direction of insertion A1 while sliding on the upper surfaces 54a of the engagement projections 54.

As illustrated in FIG. 3, when the engagement portion 61 of the main body portion 22 passes over the engagement projections 54 of the needle member 2, the engagement projections 54 fit the engagement depression 62 of the main body portion 22. Accordingly, the main body portion 22 of the movable member 3 and the holding portion 12 of the needle member 2 interfere in the longitudinal direction A. In other words, the needle member 2 and the movable member 3 are integrally movable in the longitudinal direction A. Specifically, when the movable member 3 is moved in the direction of removal A2, the inner surface of the engagement depression 62 of the main body portion 22 of the movable member 3 in the direction of insertion A1 comes into attachment with the outer surfaces of the engagement projection 54 of the holding portion 12 of the needle member 2 in the direction of insertion A1. Accordingly, the needle member 2 and the movable member 3 can be united and moved together in the direction of removal A2. Therefore, as illustrated in FIG. 4, when removing the needle portion 11 from the living body, the movable portion 21 in the needle portion 11 can be removed from the living body together with the needle portion 11.

Examples of the material of the main body portion 22 include a resin material. Examples of the resin material include: thermoplastic resins used in injection molding such as ABS resin, AS resin, polyethylene, polypropylene, polystyrene, polyvinyl chloride, polyvinylidene chloride resin, polyphenylene oxide, thermoplastic polyurethane, polymethylene methacrylate, polyoxyethylene, fluorine resin, polycarbonate, polyamide, acetal resin, acrylic resin, and polyethylene terephthalate; and thermosetting resins such as phenol resin, epoxy resin, silicone resin, and unsaturated polyester.

The housing 4 is an exterior member configured to cover the needle member 2, the movable member 3, the biasing member 5, the controller 6, and the sensor 100a, which is described below. As illustrated in FIG. 1 to FIG. 4, the housing 4 of the present embodiment includes a cylindrical member 71 configured to cover the periphery of the needle member 2, the movable member 3, the biasing member 5, the controller 6 and the sensor 100a, described below, in the radial direction B, and a base plate 72 configured to cover an end surface of the cylindrical member 71 in the direction of insertion A1 in a state in which the needle portion 11 is in the waiting position (see FIG. 1). The base plate 72 is attachable to and detachable from the cylindrical member 71.

A surface of the base plate 72 on the side of the direction of insertion A1 constitutes an attachment surface 72a that is brought into attachment with the living body surface BS when the needle portion 11 and the sensor 100a are inserted into the living body. The base plate 72 includes a through-hole 74 that penetrates in the longitudinal direction A. When the needle portion 11 in the waiting position (see FIG. 1) moves to the insertion position (see FIG. 3), the needle portion 11 protrudes from the attachment surface 72a in the direction of insertion A1 through the through-hole 74. The attachment surface 72a is provided with an affixing portion for being implanted on the living body surface BS.

The configuration of the housing 4 is not specifically limited. In the present embodiment, the needle member 2 and the movable member 3 are movably attached to the housing 4 in the longitudinal direction A but may be movably attached to a member other than the housing 4.

In addition, although the insertion device 1 of the present embodiment includes the housing 4, a configuration without the housing 4 is also applicable. However, like the housing 4 of the present embodiment, the insertion device 1 preferably includes a member that covers at least the outside periphery of the needle portion 11 in the waiting position in the radial direction B for reducing the probability that the health care workers or the patients erroneously touch the needle portion 11.

Also, although the housing 4 of the present embodiment is configured such that the cylindrical member 71 and the base plate 72 are attachable and detachable, it is not limited thereto, and both members may be formed integrally to each other. However, by configurating both members attachable and detachable, the size of a portion to be implanted on the living body surface BS can easily be reduced so that the burden of the subject can be alleviated.

Examples of the material of the housing 4 include a resin material. Examples of the resin material include: thermoplastic resins used in injection molding such as ABS resin, AS resin, polyethylene, polypropylene, polystyrene, polyvinyl chloride, polyvinylidene chloride resin, polyphenylene oxide, thermoplastic polyurethane, polymethylene methacrylate, polyoxyethylene, fluorine resin, polycarbonate, polyamide, acetal resin, acrylic resin, and polyethylene terephthalate; and thermosetting resins such as phenol resin, epoxy resin, silicone resin, and unsaturated polyester.

The biasing member 5 of the present embodiment is resiliently deformable in the longitudinal direction A. The biasing member 5 of the present embodiment is a coil spring that resiliently deforms in the longitudinal direction A. The coil spring as the biasing member 5 is disposed between the holding portion 12 of the needle member 2 and the base plate 72 of the housing 4. Therefore, the coil spring as the biasing member 5 of the present embodiment is subject to compression deformation by the needle portion 11 moving from the waiting position (see FIG. 1) to the insertion position (see FIG. 3). Also, by releasing a restoring force of the coil spring as the biasing member 5 in a state in which the needle portion 11 is in the insertion position (see FIG. 3), the needle portion 11 can be moved from the insertion position (see FIG. 3) in the direction of removal A2.

Therefore, in the insertion device 1 of the present embodiment, when the needle member 11 and the sensor 100a are inserted into the living body, the needle member 2 and the movable member 3 described above are moved in the direction of insertion A1 against the restoring force of the coil spring as the biasing member 5. Accordingly, as illustrated in FIG. 2 and FIG. 3, the needle member 2 and the movable member 3 moves in the direction of insertion A1 and the needle portion 11 and the sensor 100a are inserted into the living body. By releasing the pressing force in the direction of insertion A1 applied to the needle member 2 and the movable member 3 after the insertion of the needle portion 11 and the sensor 100a into the living body, the needle member 2 and the movable member 3 move in the direction of removal A2 by the restoring force of the coil spring as the biasing member 5. Accordingly, the needle portion 11 can be removed from the living body with the sensor 100a left in the living body. In the present embodiment, by the restoring force of the coil spring as the biasing member 5, the needle portion 11 returns from the insertion position (see FIG. 3) to a position (the waiting position as in the FIG. 1, for example) of being accommodated in the housing 4 again(see FIG. 4).

As described above, although the biasing member 5 of the present embodiment is composed of the coil spring, it is not limited to the coil spring, and other resilient members may be used, for example. Also, the insertion device 1 maybe configured not to include the biasing member 5.

The controller 6 is movably connected to the sensor 100a. Therefore, the controller 6 can receive detected information of the sensor 100a from the sensor 100a implanted in the living body. Also, as described above, the controller 6 analyzes the detection signal received from the sensor 100a and transmits the result of analysis to an external device such as a display apparatus as needed. The controller 6 includes a processor, a memory, and a battery. Note that the controller 6 may be provided not on the base plate 72 but on a separate transmitter, which can be combined with the base plate 72. In this case, a contact portion with respect to the transmitter is provided at the position of the controller 6 in FIG. 1 to FIG. 4 instead of the controller 6.

As illustrated in FIG. 1 to FIG. 4, the controller 6 of the present embodiment moves together with the needle portion 11 and the sensor 100a in the direction of insertion A1 when the needle portion 11 and the sensor 100a are inserted into the living body. More specifically, the controller 6 of the present embodiment is held by the needle member 2 in a state in which the needle portion 11 is in the waiting position (see FIG. 1). When the needle portion 11 moves from the waiting position (see FIG. 1) to the insertion position (see FIG. 3), the controller 6 moves together with the needle member 2 in the direction of insertion A1. When the needle portion 11 reaches the insertion position (see FIG. 3), the controller 6 engages the base plate 72 of the housing 4, and the state of being held by the needle member 2 is released. Any means such as adhesion or mechanical engagement can be employed as means for engaging the controller 6 and the base plate 72. Accordingly, the controller 6 assumes a state of being held on the base plate 72. Therefore, when the needle portion 11 is removed from the living body, that is, when the needle portion 11 returns from the insertion position to the waiting position, the needle member 2 moves in the direction of removal A2. However, the controller 6 does not move in the direction of removal A2 and remains on the base plate 72 of the housing 4.

The sensor 100a of the present embodiment is a thin diameter linear member to be accommodated in the medical device accommodation space 13 of the needle portion 11. As the sensor 100a, a member configured to detect an electric signal corresponding to an amount or concentration of the substance to be measured can be used. The sensor 100a extends in the medical device accommodation space 13 along the longitudinal direction A of the needle portion 11.

The sensor 100a may be, for example, a wire electrode having a circular cross-section. The wire electrode is accommodated in the medical device accommodation space 13 of the needle portion 11. The outer diameter of the wire electrode may be, for example, from 0.02 mm to 0.2 mm. For example, two wire electrodes; a working electrode and a reference electrode, maybe accommodated in the medical device accommodation space 13. The working electrode is formed basically of a core having a conductive surface and may be configured to include a detection portion 100b provided on an outer wall of the core and configured to detect the substance to be measured, and a protecting portion made of an insulating material coated on the outer wall of the core. Changes in electrical characteristics of the substance to be measured can be detected by the detection portion 100b. The detection portion 100b is formed on a core surface by using thin-film forming means such as dipping, electropolymerization, sputtering, and the like. A reagent that reacts specifically with the substance to be measured is applied on a surface of the working electrode. When the substance to be measured is glucose, a reagent containing glucose oxidase or a phenylboronic acid compounds is used. The reference electrode is used as a reference electrode for the working electrode described above. A single wire electrode formed by winding the reference electrode or a counter electrode in a coil shape around the working electrode is also applicable. Alternatively, three wire electrodes may be disposed in the medical device accommodation space 13. The three wire electrodes may be used to constitute the working electrode, the reference electrode, and the counter electrodes. Alternatively, the needle portion 11 itself may be used as the reference electrode or the counter electrode. Information on the substance to be measured detected by the detection portion 100b of the working electrode is transmitted to the controller 6.

Next, the details of the operation of the needle portion 11, the movable portion 21, and the sensor 100a when inserting and implanting the sensor 100a into the living body by using the insertion device 1 will be described. FIG. 7A is a cross-sectional view taken along the line I-I in FIG. 5 illustrating the needle portion 11, the movable portion 21, and the sensor 100a as the medical device 100 in the state in which the needle portion 11 is in the waiting position (see FIG. 1). FIG. 7B is a drawing illustrating the needle portion 11, the movable portion 21, and the sensor 100a in the state in which the needle portion 11 is in the course of moving from the waiting position (see FIG. 1) to the insertion position (see FIG. 3). FIG. 7C is a drawing illustrating the needle portion 11, the movable portion 21, and the sensor 100a in the state in which the needle portion 11 is in the insertion position (see FIG. 3). FIG. 7D is a drawing illustrating the needle portion 11, the movable portion 21, and the sensor 100a in the state in which the needle portion 11 is in the course of returning into the housing 4 after the sensor 100a has been implanted in the insertion position (see FIG. 3). FIG. 7B to FIG. 7D are all cross-sectional views like FIG. 7A.

As illustrated in FIG. 7A, in the state in which the needle portion 11 is in the waiting position (see FIG. 1), part of the sensor 100a as the medical device 100 is fixedly adhered to the sidewall portion 15. Specifically, the sensor 100a and the sidewall portion 15 are fixedly adhered in the adhered region D located on the proximal side of the detection portion 100b. Accordingly, even when the sensor 100a has a small diameter, the detection portion 100b of the sensor 100a is held without protruding from a U-shaped needle slit 20a of the needle portion 11.

As illustrated in FIG. 1 to FIG. 3, the needle member 2 and the movable member 3 both move in the direction of insertion A1 in the course of movement of the needle portion 11 from the waiting position (see FIG. 1) to the insertion position (see FIG. 3). As illustrated in FIG. 1 to FIG. 3, the relative positional relationship between the needle member 2 and the movable member 3 in the longitudinal direction A varies in the course of movement of the needle portion 11 from the waiting position (see FIG. 1) to the insertion position (see FIG. 3). In other words, the needle member 2 and the movable member 3 both move in the direction of insertion A1 in the course of movement of the needle portion 11 from the waiting position (see FIG. 1) to the insertion position (see FIG. 3), and the movable member 3 moves also relatively to get closer to the needle member 2 in the direction of insertion A1. Therefore, as illustrated in FIG. 7B, the movable portion 21 of the movable member 3 moves in the direction of insertion A1 with respect to the needle portion 11 of the needle member 2 in the course of movement of the needle portion 11 from the waiting position (see FIG. 1) to the insertion position (see FIG. 3). At this time, the cutting edge 21e of the movable portion 21 comes into contact with the proximal side of the adhered region D so that the adhered region is cut on the proximal side of the adhered region D. Further, the cutting edge 21e of the movable portion 21 moves in the direction of insertion A1 so that the adhered region D is cut from the proximal side toward the distal side. Accordingly, the sensor 100a is separated from the sidewall portion 15. In this manner, FIG. 7B illustrates the state in which the adhered state between the sensor 100a and the sidewall portion 15 is broken by the movable portion 21 and thus the sensor 100a is separated from the sidewall portion 15.

After adhesion between the sensor 100a and the sidewall portion 15 is cut, the movable member 3 moves relatively to further get closer to the needle member 2 in the direction of insertion A1, and the positional relationship as illustrated in FIG. 7C is achieved in the insertion position (see FIG. 3).

When the needle portion 11 returns from the insertion position (see FIG. 3) to the position of being accommodated in the housing 4 (for example, in the same waiting position as in FIG. 1) again by the restoring force of the coil spring as the biasing member 5, the needle portion 11 is removed from the living body together with the movable portion 21 with the sensor 100a remained in the living body as illustrated in FIG. 7D.

In the insertion device 1 according to the present embodiment, the state of adhesion between the medical device 100 and the sidewall portion 15 is released when the medical device 100 reaches a predetermined depth in the living body. This makes it easier to implant the medical device 100 at a predetermined depth in the living body.

Second Embodiment

FIG. 8 is a perspective view illustrating the needle portion 11 of the needle member 2, the movable portion 21 of the movable member 3, and the sensor 100a in an insertion device according to a second embodiment different from the insertion device 1 described above. A configuration according to the second embodiment will be described while omitting the description for the same points as the first embodiment as needed. For example, in the second embodiment, a configuration of the sensor 100a as the medical device 100 is the same as that in the first embodiment, and thus description of the details will be omitted.

A schematic configuration of the insertion device according to the present embodiment is the same as the insertion device 1 of the first embodiment. Therefore, when the insertion device of the present embodiment is not distinguished from the insertion device 1 of the first embodiment, it is referred simply as "insertion device 1" and FIG. 1 to FIG. 7 are referred to accordingly. In the second embodiment, the shape of the needle portion 11 is different from that in the first embodiment. FIG. 9 is a cross-sectional view of the needle portion 11, the movable portion 21, and the medical device 100 illustrated in FIG. 8, taken along the line II-II orthogonal to the longitudinal direction A. FIG. 10A is a cross-sectional view taken along a line in FIG. 8 illustrating the needle portion 11, the movable portion 21, and the medical device 100 in a state in which the needle portion 11 of the insertion device 1 illustrated in FIG. 1 is in the waiting position.

In the present embodiment, the needle portion 11 is formed of a wall portion 16 into a tubular shape extending along the longitudinal direction A. The needle portion 11 includes an opening portion (slit) 24 having a width that allows the medical device 100 to be detached at the distal side. In the present embodiment, the wall portion 16 includes a loading surface on part of an outer peripheral surface for placing part of the medical device 100. Specifically, in the present embodiment, the outer peripheral surface of the wall portion 16 is formed into a substantially crescent shape in cross-sectional view orthogonal to the longitudinal direction A as illustrated in FIG. 9, and a depressed surface in the wall portion 16 constitutes a loading surface 17.

In the present embodiment, the loading surface 17 is not provided at the distal end of the needle portion 11, as illustrated in FIG. 8. As illustrated in FIG. 10A, on the distal side where the loading surface 17 is not provided, part of the sensor 100*a* is fixed to the needle portion 11. Specifically, part of the sensor 100*a* is fixed on an inner peripheral surface of the wall portion 16 on the distal side where the loading surface 17 is not provided. Part of the sensor 100*a* is fixedly adhered, for example, by the adhesive agent. In the present embodiment, a portion of the sensor 100*a* on the proximal side of the detection portion 100*b* is fixedly adhered to the inner peripheral surface of the wall portion 16. A region where the sensor 100*a* and the inner peripheral surface of the wall portion 16 are fixedly adhered is indicated as an adhered region D in FIG. 10A.

At least part of the sensor 100*a* that is not adhered to the needle portion 11 is placed on the loading surface 17. In the present embodiment, the portion of the sensor 100*a* on the proximal side of the adhered region D is placed on the loading surface 17. The needle portion 11 having the loading surface 17 makes the sensor 100*a* easy to be placed stably on the needle portion 11. The needle portion 11 is fixedly adhered to the adhered region D and is inserted into the living body together with the sensor 100*a* placed on the loading surface 17.

The wall portion 16 defines the movable portion accommodation space 18 for accommodating the movable portion 21 in an interior of the tubular shaped needle portion 11. The movable portion 21 is slidable in the movable portion accommodation space 18. The movable portion accommodation space 18 extends along the longitudinal direction A. In the present embodiment, the movable portion accommodation space 18 is formed into a substantially crescent shape in cross-sectional view orthogonal to the longitudinal direction A as illustrated in FIG. 9. Specifically, the wall portion 16 is formed to have a substantially uniform thickness, and the movable portion accommodation space 18 is formed into the same shape as the outer peripheral surface of the wall portion 16.

As illustrated in FIG. 8 and FIG. 10A, the wall portion 16 is provided at the distal end thereof with a cutting edge 16*a* by a cutting surface 16*b*. In the wall portion 16 of the present embodiment, a cutting edge is formed at a position on the wall portion 16 facing a portion at the distal end where the loading surface 17 is formed (a lower position in FIG. 9 and FIG. 10A, hereinafter, referred to as "lower wall portion"). The wall portion 16 of the present embodiment has a configuration including one cutting surface having a distal end surface inclined with respect to the longitudinal direction A, but the shape of the cutting edge is not specifically limited.

In the present embodiment, a portion of the sensor 100*a* on the proximal side of the detection portion 100*b* is fixedly adhered to the wall portion 16. This allows the sensor 100*a* to be inserted into the living body together with the needle portion 11. Therefore, the sensor 100*a* may be inserted to a desired depth in the living body.

Examples of the material of the needle portion 11 that can be used include a metallic material such as stainless steel, aluminum, aluminum alloy, titanium, titanium alloy, and magnesium alloy in the same manner as the first embodiment. Also, the proximal side of the needle portion 11 is held by the holding portion 12 in the same manner as the first embodiment. The needle portion 11 can be manufactured by press work.

The movable portion 21 is movable relatively with respect to the needle portion 11 in the medical device accommodation space 13 in the direction of insertion A1 of the needle portion 11. The movable portion 21 cuts the adhered region D between the medical device 100 and the needle portion 11 by moving in the direction of insertion A1 with respect to the needle portion 11. Specifically, the distal end of the movable portion 21 comes into contact with the proximal side of the adhered region D so that the adhesion is broken on the proximal side of the adhered region D. Further, the cutting edge 21*e* of the movable portion 21 moves in the direction of insertion A1 so that the medical device 100 is separated from the sidewall portion 15 from the proximal side toward the distal side of the adhered region D. Accordingly, the adhered state between the medical device 100 and the needle portion 11 is released, and thus the medical device 100 is separated from the needle portion 11. The movable portion 21 of the present embodiment moves in the direction of insertion A1 with respect to the needle portion 11 to bring the cutting edge 21*e* that constitutes the distal end of the movable portion 21 into contact with the adhered region D. From this state, the movable portion 21 further moves in the direction of insertion A1 so that the adhered region D is cut toward the direction of insertion A1, and the medical device 100 is separated from the needle portion 11.

As illustrated in FIG. 8 and FIG. 10A, the movable portion 21 of the present embodiment is configured as a member extending along the longitudinal direction A in the movable portion accommodation space 18. Specifically, in the present embodiment, the cross section is formed into a curved plate shape in conformity with the shape of the movable portion accommodation space 18 as illustrated in FIG. 9.

The movable portion 21 includes the cutting edge 21*e* formed at the distal end thereof. More specifically, the movable portion 21 of the present embodiment has a configuration including one cutting surface inclined with respect to the longitudinal direction A, but the shape of the cutting edge is not specifically limited. When the movable portion 21 moves in the direction of insertion A1 with respect to the needle portion 11, the cutting edge 21e comes into contact with the adhered region D, and further, the movable portion 21 enters between the medical device 100 (sensor 100a) and the needle portion 11 to break the adhered region D. This separates the sensor 100a and the needle portion 11.

Examples of the material of the movable portion 21 that can be used include a metallic material such as stainless steel, aluminum, aluminum alloy, titanium, titanium alloy, and magnesium alloy in the same manner as the first embodiment. Also, the end portion of the movable portion 21 in the direction of removal A2 is held by the main body portion 22 in the same manner as the first embodiment. The movable portion 21 can be manufactured by plastic working. For example, the movable portion 21 can be manufactured by cutting work on a drawn tube having a predetermined inner diameter or press work on a metallic plate.

Next, the details of the operation of the needle portion 11, the movable portion 21, and the sensor 100a when inserting and implanting the sensor 100a as the medical device 100 into the living body by using the insertion device 1 in the present embodiment will be described. FIG. 10A is a cross-sectional view taken along the line III-III in FIG. 8 illustrating the needle portion 11, the movable portion 21, and the sensor 100a in the state in which the needle portion 11 is in the waiting position (see FIG. 1). FIG. 10B is a drawing illustrating the needle portion 11, the movable portion 21, and the sensor 100a in the state in which the needle portion 11 is in the course of moving from the waiting position (see FIG. 1) to the insertion position (see FIG. 3). FIG. 10C is a drawing illustrating the needle portion 11, the movable portion 21, and the sensor 100a in the state in which the needle portion 11 is in the insertion position (see FIG. 3). FIG. 10D is a drawing illustrating the needle portion 11, the movable portion 21, and the sensor 100a in the state in which the needle portion 11 is in the course of returning into the housing 4 after the sensor 100a has been implanted in the insertion position (see FIG. 3). FIG. 10B to FIG. 10D are all cross-sectional views like FIG. 10A.

As illustrated in FIG. 10A, in the state in which the needle portion 11 is in the waiting position, part of the sensor 100a as the medical device 100 is fixedly adhered to the inner peripheral surface of the wall portion 16. Specifically, the sensor 100a and the wall portion 16 are fixedly adhered in the adhered region D on the proximal side of the detection portion 100b. The adhesive agent and the fixedly adhering method are the same as those in the first embodiment.

As illustrated in FIG. 1 to FIG. 3, the needle member 2 and the movable member 3 both move in the direction of insertion A1 in the course of movement of the needle portion 11 from the waiting position (see FIG. 1) to the insertion position (see FIG. 3). As illustrated in FIG. 1 to FIG. 3, the relative positional relationship between the needle member 2 and the movable member 3 in the longitudinal direction A varies in the course of movement of the needle portion 11 from the waiting position (see FIG. 1) to the insertion position (see FIG. 3). In other words, the needle member 2 and the movable member 3 both move in the direction of insertion A1 in the course of movement of the needle portion 11 from the waiting position (see FIG. 1) to the insertion position (see FIG. 3), and the movable member 3 moves also relatively to get closer to the needle member 2 in the direction of insertion A1. Therefore, as illustrated in FIG. 10B, the movable portion 21 of the movable member 3 moves in the direction of insertion A1 with respect to the needle portion 11 of the needle member 2 in the course of movement of the needle portion 11 from the waiting position (see FIG. 1) to the insertion position (see FIG. 3). At this time, the cutting edge 21e of the movable portion 21 comes into contact with the adhered region D and the adhesion between the sensor 100a and the wall portion 16 is released by the cutting edge 21e of the movable portion 21. FIG. 10B illustrates the state in which the adhesion between the sensor 100a and the wall portion 16 is released by the movable portion 21.

After adhesion between the sensor 100a and the wall portion 16 is released, the movable member 3 moves relatively to further get closer to the needle member 2 in the direction of insertion A1, and the positional relationship as illustrated in FIG. 10C is achieved in the insertion position (see FIG. 3).

When the needle portion 11 returns from the insertion position (see FIG. 3) to the position of being accommodated in the housing 4 (for example, in the same waiting position as in FIG. 1) again by the restoring force of the coil spring as the biasing member 5, the needle portion 11 is removed from the living body together with the movable portion 21 with the sensor 100a remained in the living body as illustrated in FIG. 10D.

As described above, in the insertion device 1 of the present embodiment, the state of adhesion between the medical device 100 and the sidewall portion 15 is released when the medical device 100 reaches a predetermined depth in the living body. This makes it easier to implant the medical device 100 at a predetermined depth in the living body.

The insertion device 1 according to the first embodiment and the second embodiment described above may have other configurations. For example, the insertion device 1 according to the first embodiment and the second embodiment may have a restricting mechanism that restricts the relative movement of the needle portion 11 and the movable portion 21 in directions other than the longitudinal direction A. The restricting mechanism will be described next.

FIG. 11 is a cross-sectional view taken along a line IV-IV in FIG. 7A. As illustrated in FIG. 11, when the restricting mechanism is applied to the insertion device 1 according to the first embodiment, for example, a rib 44 protruding toward the medical device accommodation space 13 is formed on an inner surface of the needle portion 11. More specifically, the rib 44 protruding toward the medical device accommodation space 13 and extending in the longitudinal direction A is formed on the inner surface of the third side plate portion 15c of the sidewall portion 15 of the needle portion 11. A receiving groove 25 extending in the longitudinal direction A is formed on an outer surface of the movable portion 21. More specifically, the receiving groove 25 extending in the longitudinal direction A is formed on an outer surface of the third groove wall portion 21c of the movable portion 21. The rib 44 fits the receiving groove 25 of the movable portion 21 and constitutes the restricting mechanism 80 together with the receiving groove 25. The rib 44 may simply be provided at least part of the needle portion 11 in the longitudinal direction A.

FIG. 12 is a cross-sectional view taken along the line V-V in FIG. 10A. As illustrated in FIG. 12, when the restricting mechanism is applied to the insertion device 1 according to the second embodiment, for example, the rib 44 protruding toward the movable portion accommodation space 18 is formed on the inner peripheral surface of the wall portion 16 that constitutes the needle portion 11. More specifically, the rib 44 protruding toward the movable portion accommodation space 18 and extending in the longitudinal direction A is formed on the inner peripheral surface side of the lower wall portion of the wall portion 16. The movable portion 21 includes the receiving groove 25 extending in the longitudinal direction A on a bottom surface side that comes into contact with the lower wall portion of the wall portion 16. The rib 44 fits the receiving groove 25 of the movable portion 21 and constitutes the restricting mechanism 80 together with the receiving groove 25. The rib 44 may simply be provided at least part of the needle portion 11 in the longitudinal direction A.

Note that the restricting mechanism 80 is not limited to the example described here, and the specific configuration is not particularly limited as long as it is configured to restrict the relative movement of the needle portion 11 and the movable portion 21 in directions other than the longitudinal direction A.

The insertion device according to the present disclosure is not limited to the specific configuration and process described in the embodiments above, and various modifications and changes can be made without departing from the scope of the appended claims.

REFERENCE CHARACTER LIST

1: insertion device
2: needle member
3: movable member
4: housing
5: biasing member
6. controller
11: needle portion
12: holding portion
13: medical device accommodation space
15: sidewall portion
15a: first side plate portion
15b: second side plate portion
15c: third side plate portion
16: wall portion
17: loading surface
18: movable portion accommodation space
16a, 19a, 21e: cutting edge
19b, 21f: cutting surface
20a: needle portion slit
20b: movable portion slit
21: movable portion
21a: first groove wall portion
21b: second groove wall portion
21c: third groove wall portion
22: main body portion
23: groove space
24: opening portion
25: receiving groove
44: rib
51: main body portion
51a: holding opening
52: locking claw portion
53: extending portion
54: engagement projection
54a: upper surface
61: engagement portion
62: engagement depression
71: cylindrical member
72: base plate
72a: attachment surface
74: through-hole 80: restricting mechanism
100: medical device
100a: sensor
100b: detection portion
100e: end portion
A: longitudinal direction of needle portion
A1: direction of insertion
A2: direction of removal
B: radial direction of needle portion
BS: living body surface
D: adhered region

The invention claimed is:

1. An insertion device for inserting a medical device into a living body, comprising:
   a needle portion to which at least part of the medical device is adhered and configured to be inserted into the living body together with the adhered medical device, wherein the needle portion internally defines a medical device accommodation space that accommodates the medical device; and
   a movable portion that is movable with respect to the needle portion in a direction of insertion of the needle portion, wherein the movable portion has a groove space extending along the direction of insertion that is located within the medical device accommodation space and accommodates the medical device, wherein:
   the movable portion is configured to move in the direction of insertion with respect to the needle portion to cut an adhered region between the medical device and the needle portion and separate the medical device and the needle portion.

2. The insertion device according to claim 1, wherein:
   the needle portion comprises a sidewall portion that defines the medical device accommodation space, and the medical device is adhered to an inner surface of the sidewall portion.

3. The insertion device according to claim 1, comprising a restricting mechanism configured to restrict relative movement of the needle portion and the movable portion in directions other than the longitudinal direction of the needle portion.

4. An insertion device for inserting a medical device into a living body, comprising:
   a needle portion configured to be inserted into the living body together with the medical device, wherein the needle portion comprises a sidewall portion that defines a medical device accommodation space that accommodates the medical device, and wherein the medical device is adhered to an inner surface of the sidewall portion; and
   a movable portion that is movable with respect to the needle portion in a direction of insertion of the needle portion, wherein the movable portion has a groove space extending along the direction of insertion that is located within the medical device accommodation space and accommodates the medical device,
   wherein the movable portion is configured to move in the direction of insertion with respect to the needle portion to cut an adhered region between the medical device and the needle portion and separate the medical device and the needle portion.

5. A method for inserting a medical device into a living body, the method comprising:
   providing an insertion device comprising:
      a needle portion to which at least part of the medical device is adhered, wherein the needle portion internally defines a medical device accommodation space that accommodates the medical device, and a movable portion that is movable with respect to the needle portion in a direction of insertion of the needle portion, wherein the movable portion has a groove space extending along the direction of insertion that is located within the medical device accommodation space and accommodates the medical device; and inserting, into a living body, the needle portion together with the adhered medical device, which causes the movable portion to move in the direction of insertion with respect to the needle portion to cut an adhered region between the medical device and the needle portion and separate the medical device and the needle portion.

6. An insertion device for inserting a medical device into a living body, comprising:

a needle portion to which at least part of the medical device is adhered and configured to be inserted into the living body together with the adhered medical device; and a movable portion that is movable with respect to the needle portion in a direction of insertion of the needle portion, wherein:

the movable portion is configured to move in the direction of insertion with respect to the needle portion to cut an adhered region between the medical device and the needle portion and separate the medical device and the needle portion, the needle portion comprises a wall portion that has a tubular shape extending along the direction of insertion, the wall portion internally includes a movable portion accommodation space that accommodates the movable portion, and the wall portion has a loading surface on portion of an outer peripheral surface for placing at least a portion of the medical device that is not adhered to the needle portion.

7. The insertion device according to claim 6, comprising a restricting mechanism configured to restrict relative movement of the needle portion and the movable portion in directions other than the longitudinal direction of the needle portion.

* * * * *